United States Patent [19]

Moubayed et al.

[11] Patent Number: 5,536,475
[45] Date of Patent: Jul. 16, 1996

[54] APPARATUS FOR MAGNETIC CELL SEPARATION

[75] Inventors: Ahmad-Maher Moubayed, Mission Viejo; R. Alan Hardwick, Lake Forest, both of Calif.

[73] Assignee: Baxter International Inc., Deerfield, Ill.

[21] Appl. No.: 212,479

[22] Filed: Mar. 14, 1994

Related U.S. Application Data

[63] Continuation-in-part of Ser. No. 187,417, Jan. 25, 1994, abandoned, which is a continuation-in-part of Ser. No. 979,360, Nov. 20, 1992, abandoned, which is a continuation of Ser. No. 397,087, Aug. 22, 1989, abandoned, which is a continuation-in-part of Ser. No. 255,214, Oct. 11, 1988, abandoned.

[51] Int. Cl.⁶ .......................... G01N 33/553; B01L 11/00
[52] U.S. Cl. .......................... 422/101; 209/217; 209/225; 209/232; 210/222; 422/44; 422/99; 435/2; 435/7.21; 435/962; 435/971; 436/526; 436/806; 436/807; 604/6
[58] Field of Search .............................. 422/44, 99, 101; 436/526, 806, 807, 177, 178; 435/2, 7.21, 7.24, 7.23, 7.25, 962, 971; 604/5, 6; 210/222, 223, 695; 209/217, 221, 224, 225, 232

[56] References Cited

U.S. PATENT DOCUMENTS

| | | |
|---|---|---|
| 3,970,518 | 7/1976 | Giaever . |
| 4,018,886 | 4/1977 | Giaever . |
| 4,141,687 | 2/1979 | Forrest . |
| 4,177,253 | 12/1979 | Davies et al. . |
| 4,190,524 | 2/1980 | Watson . |
| 4,219,411 | 8/1980 | Yen . |
| 4,230,685 | 10/1980 | Senyei . |
| 4,272,510 | 6/1981 | Smith et al. . |
| 4,290,528 | 9/1981 | Stekly . |
| 4,356,967 | 11/1982 | Lunick .................... 422/104 |
| 4,375,407 | 3/1983 | Kronick . |
| 4,452,773 | 6/1984 | Molday . |
| 4,454,234 | 6/1984 | Czerlinski . |

(List continued on next page.)

FOREIGN PATENT DOCUMENTS

| | | |
|---|---|---|
| 260280B1 | 5/1992 | European Pat. Off. . |
| WO91/16116 | 10/1991 | WIPO . |
| WO91/16088 | 10/1991 | WIPO . |
| WO92/07243 | 4/1992 | WIPO . |
| WO93/08258 | 4/1993 | WIPO . |

OTHER PUBLICATIONS

Kvalheim et al, "Immunomagnetic removal of B–lymphonal cells from human bone marrow: a procedure for clinical use" Bone Marrow Transplantation, vol. 3 pp. 31–41 (1988).
Hardwick et al *Artificial Organs* 14:342–347, 1990.
Hardwick et al *J. Hematotherapy* 1:379–386, 1992.
Hardwick et al *Advances in Bone Marrow Purging and Processing*, pp. 583–589, 1992.

*Primary Examiner*—Jill Warden
*Assistant Examiner*—Jan M. Ludlow
*Attorney, Agent, or Firm*—Poms Smith Lande & Rose; Janice Guthrie; Michael Schiffer

[57] ABSTRACT

An apparatus for magnetic cell separation using paramagnetic microbeads includes a base upon which is movably carried a rocker member. The rocker member carries both a primary processing container in which a mixture of liquid with cells and paramagnetic microbeads is received; and a primary magnet movable from a first position adjacent to the primary container to magnetically capture the microbeads, and a second position spaced from the primary container to magnetically release the microbeads. The mixture of liquid with cells and microbeads is agitated by tilting motions of the rocker assembly, thereby achieving the binding of target cells to microbeads. The paramagnetic microbeads, with bound target cells, are captured and released by movements of the primary magnet between its first and second positions. A secondary magnet is placed downstream from the primary magnet to capture any paramagnetic microbeads which might escape from the primary magnet. Also provided is an interconnected container apparatus for use to contain and appropriately conduct the liquid, cells, and microbeads.

22 Claims, 6 Drawing Sheets

U.S. PATENT DOCUMENTS

| | | |
|---|---|---|
| 4,554,088 | 11/1985 | Whitehead . |
| 4,582,622 | 4/1986 | Ikeda et al. . |
| 4,595,494 | 6/1986 | Kukuck . |
| 4,628,037 | 12/1986 | Chagnon . |
| 4,664,796 | 5/1987 | Graham et al. . |
| 4,672,040 | 6/1987 | Josephson . |
| 4,695,392 | 9/1987 | Whitehead . |
| 4,710,472 | 12/1987 | Saur et al. . |
| 4,738,773 | 4/1988 | Muller-Ruchholtz . |
| 4,751,053 | 6/1988 | Dodin . |
| 4,777,145 | 10/1988 | Luotola et al. . |
| 4,855,045 | 8/1989 | Reed . |
| 4,861,553 | 8/1989 | Mawhirt et al. ............................ 422/65 |
| 4,904,391 | 2/1990 | Freeman . |
| 4,910,148 | 3/1990 | Sorensen et al. . |
| 4,921,597 | 5/1990 | Lurie . |
| 4,941,969 | 7/1990 | Schonert . |
| 4,988,618 | 6/1991 | Li et al. . |
| 5,053,344 | 10/1991 | Zorowski . |
| 5,076,914 | 12/1991 | Garaschenko . |
| 5,076,950 | 12/1991 | Ullman . |
| 5,091,206 | 2/1992 | Wong et al. . |
| 5,108,933 | 4/1992 | Liberti et al. . |
| 5,158,871 | 10/1992 | Rossomando . |
| 5,183,638 | 2/1993 | Wakatake . |
| 5,200,084 | 4/1993 | Liberti . |
| 5,215,926 | 6/1993 | Etchells, III et al. ................... 436/501 |
| 5,240,856 | 8/1993 | Goffe et al. . |
| 5,336,760 | 8/1994 | Hardwick et al. ....................... 530/413 |

APPARATUS FOR MAGNETIC CELL SEPARATION

This application is a continuation-in-part of U.S. application Ser. No. 08/187,419, filed Jan. 25, 1994 now abandoned; which is a continuation-in-part of U.S. application Ser. No. 07/979,360, filed Nov. 20, 1992 now abandoned; which is a continuation of U.S. application Ser. No. 07/397,067, filed Aug. 22, 1989, now abandoned; which was a continuation-in-part of U.S. application Ser. No. 07/255,214, filed Oct. 11, 1988, now abandoned.

This application is also technically related to copending U.S. application Serial No. 08,212,616, filed concurrently herewith.

BACKGROUND OF THE INVENTION

1. Technical Field

The present invention is in the field of apparatus and method for magnetic cell separation. More particularly, magnetic separation of viable desired cells (target cells) from a heterogeneous cell mixture is accomplished by magnetic separation of desired cells from unwanted cells and other materials while the target cells are bound to paramagnetic beads, forming cell/bead complexes, followed by unbinding of the paramagnetic beads from the target cells, and removal of the paramagnetic beads from the target cells.

2. Related Technology

In the field of cell separation, it is common to separate cells from plasma in blood or bone marrow, and also to separate, by centrifugation, white cells from red cells and platelets. The white cell population separated by standard centrifugation techniques is known as the "buffy coat" fraction. The buffy coat fraction excludes hemoglobin-containing erythrocytic cells as well as platelets. However, the buffy coat fraction does contain a wide mix of hematopoietic mononuclear cells (MNC), including stem cells and progenitors of the erythrocyte, lymphocyte, monocyte, macrophage, granulocyte, and megakaryocyte lineages.

The various types of hematopoietic mononuclear cells are of nearly equal specific gravity, and thus they may not be separated from each other by centrifugation alone. However, different cell types have different sets of cell-surface markers such as specific proteins and glycoproteins on their surfaces. Thus, positive cell separation techniques may exploit selective binding to the desired cell type, also known as the "target cell".

For example, the hematopoietic stem cell is often the desired "target cell" because its progeny have the capacity to differentiate into all the different types of hematopoietic cells. In theory, it is possible to reconstitute a patient's hematopoietic system by infusing a concentrated suspension of stem cells. A stem cell marker known as "CD34 cell surface antigen" may be exploited to separate human hematopoietic stem cells from a mixture of mononuclear cells.

Once positive separation of stem cells becomes practical, new fields of therapy become possible. For instance, a patient's stem cells may be selected, induced to proliferate in an ex vivo culture, and then be returned to the patient after radiation or high dose chemotherapy treatments, which destroy the rapidly-dividing hematopoietic cells of the bone marrow. The selected stem cells may also be induced to differentiate ex vivo to produce more mature cells such as neutrophil and megakaryocyte precursors, which then may be returned to the patient in order to reduce bacterial infections and episodes of bleeding. A concentrated suspension of stem cells would also provide a natural host for gene therapy. For instance, a patient's selected stem cells could be transfected with a gene which, when expressed, could cure a genetic disease of the hematopoietic system such as sickle cell anemia or chronic granulomatous disease. Stem cells also could be transfected with genes which could cure genetic diseases outside of the hematopoietic system. For instance, certain forms of hemophilia could be cured if a small number of the patients' stem cells could be made to produce only a very small amount of certain clotting factors. Also, adjunct cancer therapies are envisioned whereby a patient's stem cells are transfected with a gene which provides resistance to chemotherapeutic agents. After these transfected stem cells repopulate the patient's bone marrow, the patient may be given high-dose chemotherapy for metastatic breast or colon cancer, for instance. The chemotherapeutic drugs will target rapidly dividing metastatic cancer cells, but hematopoietic cells of the bone marrow will be spared because they express a gene which disables the drugs.

The field of cell separation has been divided into two general categories: negative cell separation and positive cell separation. In negative cell separation, the cells that are bound in the device are deleterious cells such as tumor cells that are to be purged from a heterogeneous cell mixture such as blood or bone marrow, and which subsequently is returned to the patient. Thus, in negative separation, it is not critical to maintain the viability of the bound cells. Rather, in negative separation, it is critical to remove 100% of the tumor cells while maintaining the viability of the unbound cells.

Positive cell separation presents special challenges in that it is critical to maintain the viability of the bound cells. One approach to positive cell separation involves the use of an avidin column to which biotinylated secondary antibodies are bound, as may be seen in the following publication, EP 260 280 B1; WO 92/07243; WO 91/16116; WO 91/16088; WO 93/08258.

The heterogeneous cell mixture is first incubated with primary antibodies against CD34, for instance, which specifically binds to stem cells. The cell mixture then flows through the column such that the secondary antibodies on the column bind to the primary antibodies, which in turn are bound to the desired cells. The undesired cells travel through the column with the elution fraction for subsequent disposal. U.S. Pat. No. 5,240,856 (Goffe, et al.), discloses the use of a magnetic stir bar to mix the cell suspension during column processing. The positively selected cells are then mechanically dislodged from the column. However, there are problems associated with this column-based system such as low cell viability, possibly due to mechanical damage; and of low cell purity and yield, possibly due to entrapping of the cells in the column.

Other current practices in the field for cell separation utilize matrix materials of, for example, hollow fibers, flat sheet membrane, or packed-bed bead or particle materials with physically adsorbed or covalently attached chemicals or antibodies for selective cell separation. These devices are designed to allow continuous whole blood or blood component inflow and return. Since these devices operate at normal blood flow rates under conditions in which the concentration of desired cells can be very low compared with other cell types, the separation process is often not efficient. Moreover, with these systems it is difficult to collect the selected cells in a viable state.

The development of paramagnetic beads offered the prospect of magnetic separation of target cells. Various methods to produce magnetic and paramagnetic particles are disclosed in the following United States patents: U.S. Pat. No. 4,672,040 (Josephson); U.S. Pat. No. 5,091,206 (Wong, et al); U.S. Pat. No. 4,177,253 (Davies, et al); U.S. Pat. No. 4,454,234 (Czerlinski); U.S. Pat. No. 4,582,622 (Ikeda, et al); U.S. Pat. No. 4,452,773 (Molday); U.S. Pat. No. 5,076,950 (Ullman); U.S. Pat. No. 4,554,088 (Whitehead); and U.S. Pat. No. 4,695,392 (Whitehead).

Various methods were devised to use magnetic particles for assays. See, for example, United States patents: U.S. Pat. No. 4,272,510 (Smith, et al); U.S. Pat. No. 4,777,145 (Luotola, et al); U.S. Pat. No. 5,158,871 (Rossomando); U.S. Pat. No. 4,628,037 (Chagnon); U.S. Pat. No. 4,751,053 (Dodin); U.S. Pat. No. 4,988,618 (Li, et al); U.S. Pat. No. 5,183,638 (Wakatake); U.S. Pat. No. 4,018,886 (Giaever); and U.S. Pat. No. 4,141,687 (Forrest).

Attempts were made to use magnetic particles for separation of biological components, including cells. The following is a list of United States patents known to the Applicants and believed to be directed to magnetic separators and methods: U.S. Pat. No. 4,855,045 (Reed); U.S. Pat. No. 4,664,796 (Graham, et al.); U.S. Pat. No. 4,190,524 (Watson); U.S. Pat. No. 4,738,773 (Müller-Ruchholtz); U.S. Pat. No. 4,941,969 (Schönert); U.S. Pat. No. 5,053,344 (Zhorowski); U.S. Pat. No. 5,200,084 (Liberti); U.S. Pat. No. 4,375,407 (Kronick); U.S. Pat. No. 5,076,914 (Garaschenko); U.S. Pat. No. 4,595,494 (Kukuck); U.S. Pat. No. 4,290,528 (Stekly); U.S. Pat. No. 4,921,597 (Lurie); U.S. Pat. No. 5,108,933 (Liberti, et al.); U.S. Pat. No. 4,219,411 (Yen); U.S. Pat. No. 3,970,518 (Giaever); and U.S. Pat. No. 4,230,685 (Senyei). All of these devices and methods have met with very limited success due to problems with efficiency of cell separation and retention, and low viability of processed cells.

In attempts to remedy the problems with cell separation, other researchers devised alternate magnetic separator devices, as evidenced by the following United States patents, which proposed, for example, adjustable magnet positions (U.S. Pat. No. 4,710,472; Saur, et al), magnetic gradients (U.S. Pat. No. 4,904,391; Freeman), and magnets of opposite polarity (U.S. Pat. No. 4,910,148; Sorensen, et al). These proposed devices did not solve the two main problems generally encountered in magnetic negative and positive cell separation, i.e., first, the need for very high target cell separation which desirably approaches 100% from a heterogeneous population containing a very low percentage of target cells; and second, the need for removal of nearly all the paramagnetic beads from the final cell product. Thus, these proposed conventional magnetic separator devices did not meet with much success for either negative or positive cell separation.

The central problems for both negative and positive cell separation as described above were solved by utilizing two different magnets in series (Hardwick, et al., *Artificial Organs* 14:342–347, 1990; co-pending U.S. patent applications Ser. No. 07/979,360 and Ser. No. 07/972,072). In this invention, the first magnet has a relatively strong surface magnetic field strength combined with a broad "reach out" capacity such that its magnetic attractive force acts across the depth of the first container to magnetically attract and bind a high proportion of the paramagnetic particles in the first container. The second magnet in the series has a much stronger magnetic field strength at its surface than the first magnet, such that any paramagnetic beads which escape the first magnet are captured by the second magnet, and thus are removed from the final cell suspension product.

This invention by Hardwick, et al., solved the central problems for cell separation, in general, and for negative cell separation in particular. However, positive cell separation posed an additional challenge in that a greater yield of viable selected cells was desired. Positive cell separation was made practical by inventive changes in the first magnet and in the first container such that desired cells are not crushed as they are drawn on paramagnetic beads to the first magnet (See, "Design of Large-Scale Separation Systems for Positive and Negative Immunomagnetic Selection of Cells Using Superparamagnetic Mircospheres", Hardwick, et al., *J. Hematotherapy* 1:379–386, 1992, first mailing date to subscribers Jan. 25, 1993). The subject matter of this publication is covered in co-pending United States patent application Ser. No. 08/187,419, filed Jan. 25, 1994 now abandoned. The preferred first magnet for positive cell separation retains certain of the characteristics of the first magnet for negative cell separation in that its "reach out" capacity is sufficiently broad to magnetically attract paramagnetic beads across the depth of the first container. However, the first magnet for positive cell separation has a much lower magnetic field strength at its surface than does the first magnet used for negative cell separation. Moreover, the first container for positive cell separation is noncollapsible. This combination of first magnet and non-collapsible first container permits a much greater yield of viable desired cells. In positive as well as negative cell separation, the second magnet has a much stronger magnetic field strength at its surface than the first magnet.

The system for positive cell separation described immediately above is manually operated, and may be considered somewhat labor intensive. As with all manual systems, the results obtained depend greatly upon the skill of the operator, and may not be as repeatable as is desired. There remains a need for a positive cell separation apparatus which is suitable for a clinical laboratory with limited available labor. Such an apparatus would preferably be semi-automated such that the operator would be free to attend to other duties during most of the cell separation procedure. Also, this semi-automated apparatus would improve the reliability and repeatability of the positive cell separation process by insuring that the operator performs the complex cell separation process correctly each time. Also, the repeatability of the process and quality of results would be improved by such a semi-automated apparatus because the performance of the many steps in the process would be less dependent upon operator skill level, and less affected by the level of the operator's attention to the process.

Accordingly, a primary object for this invention is to provide a semi-automated apparatus for magnetic cell separation.

Another object for the present invention is to provide such an apparatus which includes a semi-automated machine; and a disposable apparatus set in which the cell solution and materials for cell separation are handled and contained during the process. This disposable apparatus set is configured for use with the semi-automated machine, but is fully discarded after one use to avoid contact of laboratory personnel with potentially hazardous biological materials. The single-use disposable set also avoids cross-contamination between patients' blood samples.

Yet another object for the present invention is to provide such a disposable apparatus set in which all of the interconnections of the conduits and chambers of the apparatus set are permanently and fully sealed. This permanent sealing of the apparatus set further insures against contact of laboratory personnel with potentially hazardous biological materials, and improves the purity and sterility of the resulting product of separated target cells.

These and other objects and advantages of the present invention will be apparent from a reading of the following detailed description of a single exemplary preferred embodiment of the invention, taken in conjunction with the appended drawing Figures, in which the same reference numeral refers to the same feature throughout the drawing Figures, or to features which are analogous in structure or function.

BRIEF DESCRIPTION OF THE DRAWING FIGURES

FIG. 1 provides a front quarter perspective view of a combined magnetic cell separation apparatus according to the present invention, which combined apparatus includes a semi-automatic machine, and a disposable apparatus set of processing chambers with permanently interconnecting tubing and associated valves and fittings;

FIG. 2 provides a view of the disposable apparatus set of the present invention for use with the machine of FIG. 1, shown laid out as though on a table to better depict the structure and interconnection of the various parts of the disposable apparatus set;

FIG. 3 is a diagrammatic representation of the mechanism, motors, control circuits, and operator input/output facilities of the machine seen in FIG. 1;

FIG. 4 provides a fragmentary cross sectional view taken generally at the plane 4—4 of FIG. 1;

Figure 1:
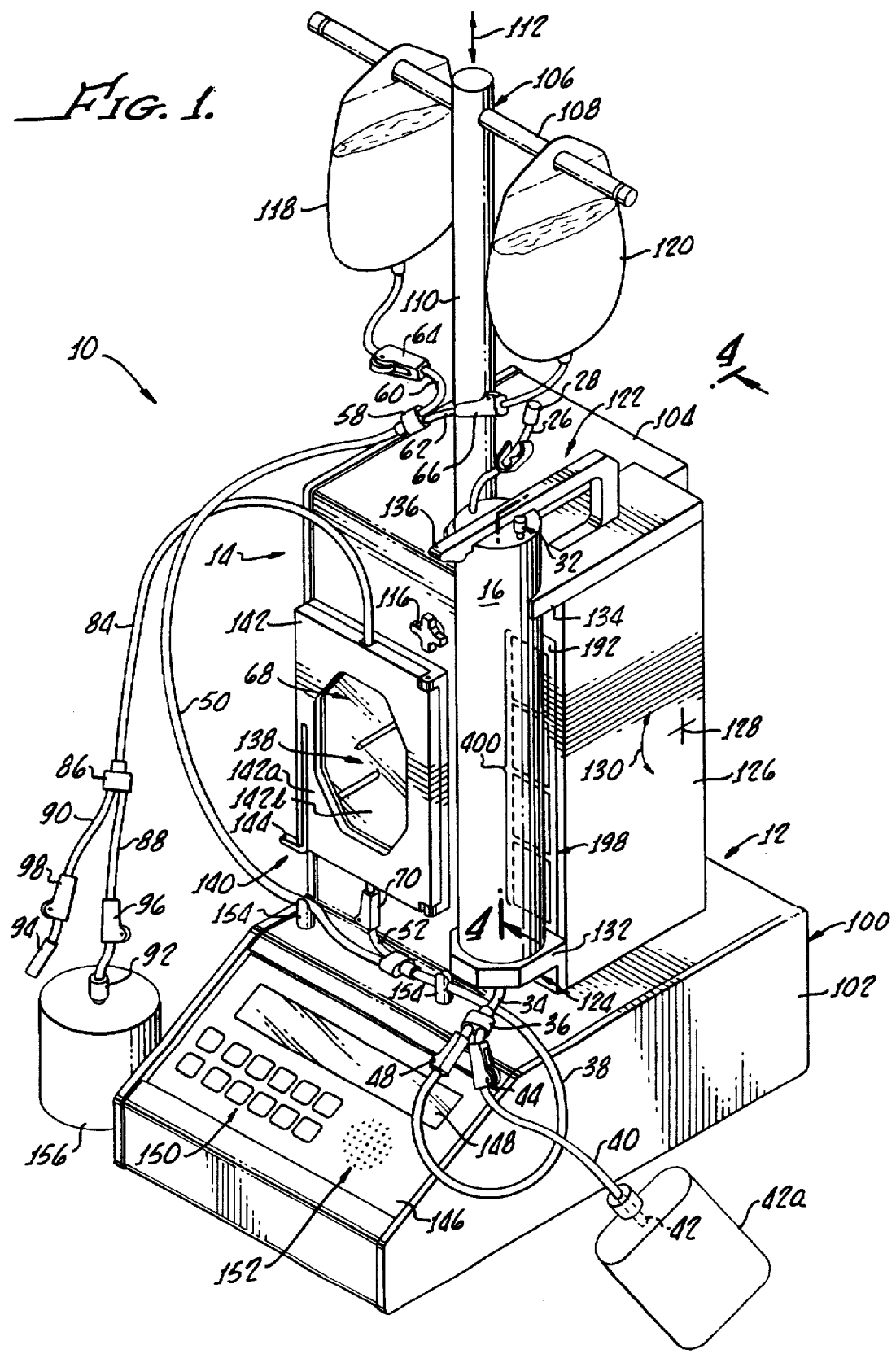
Figure 2:
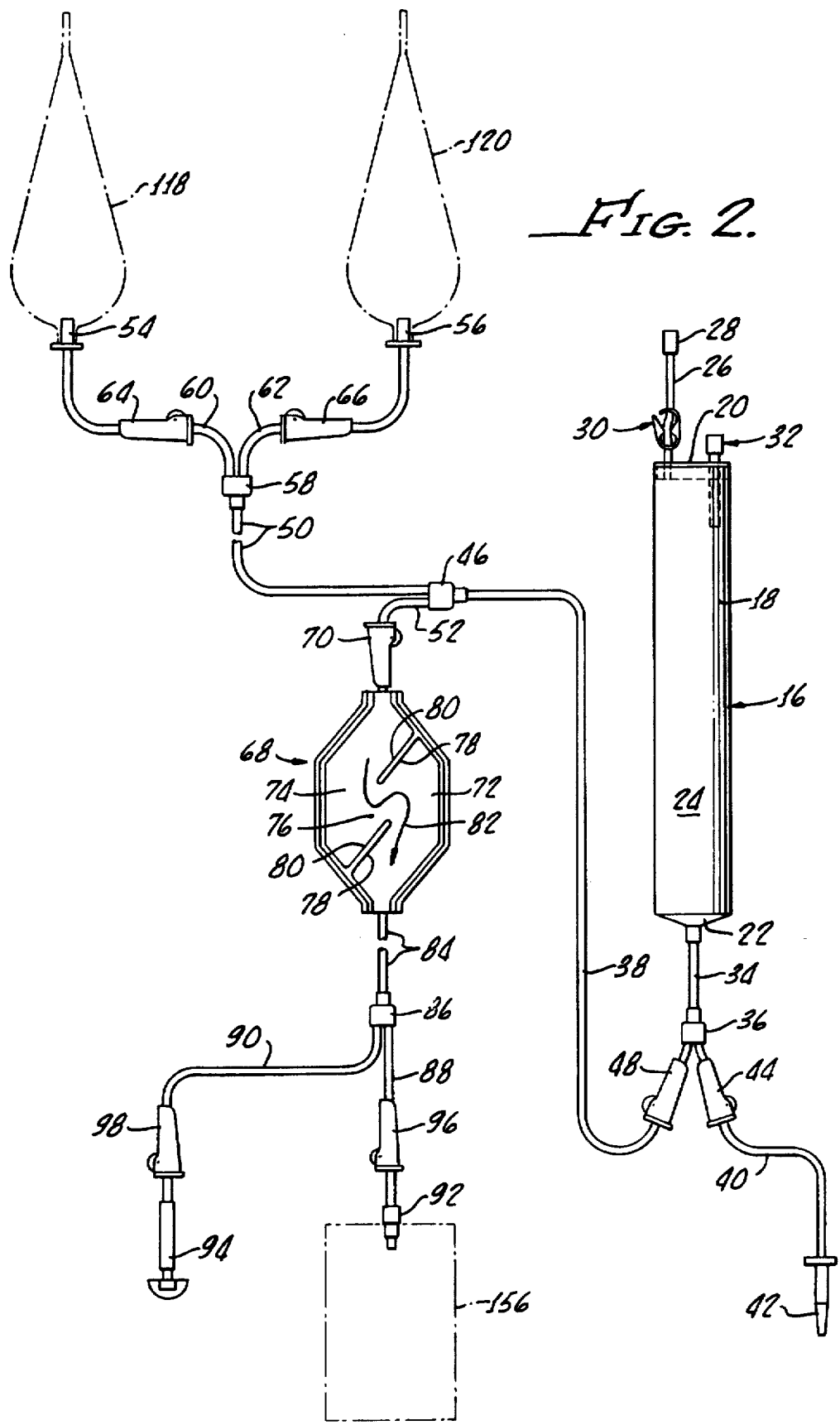
Figure 7:
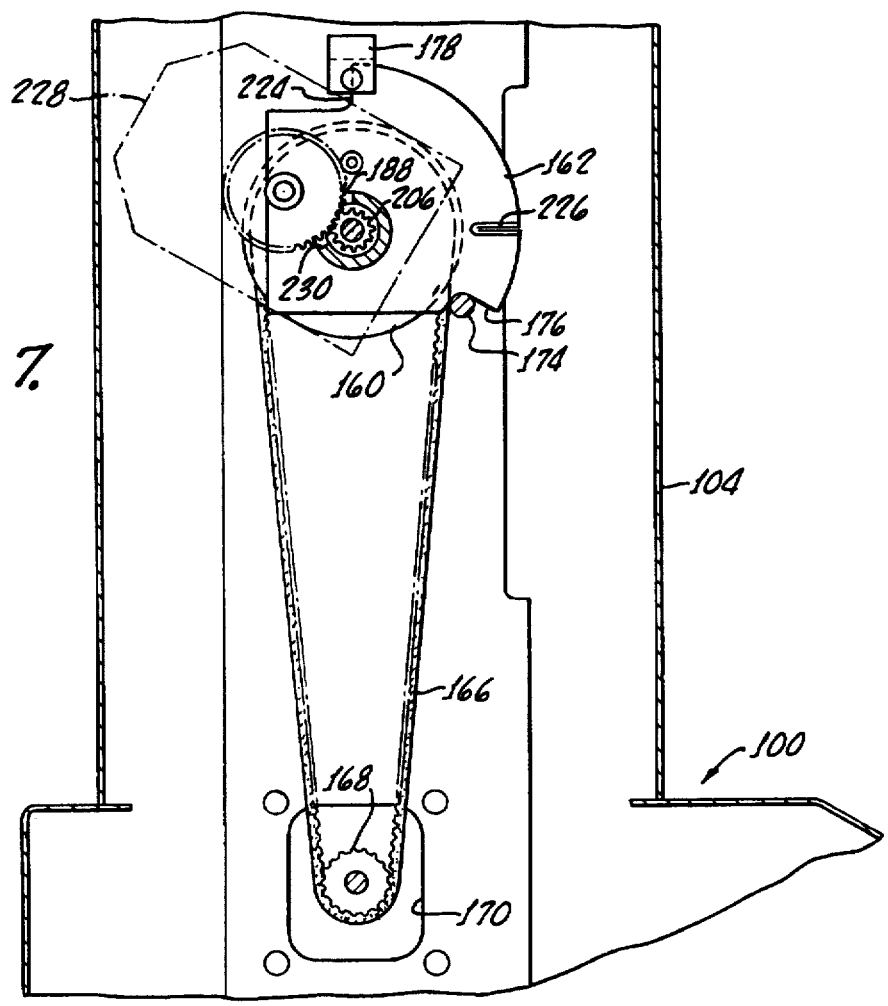
Figure 8:
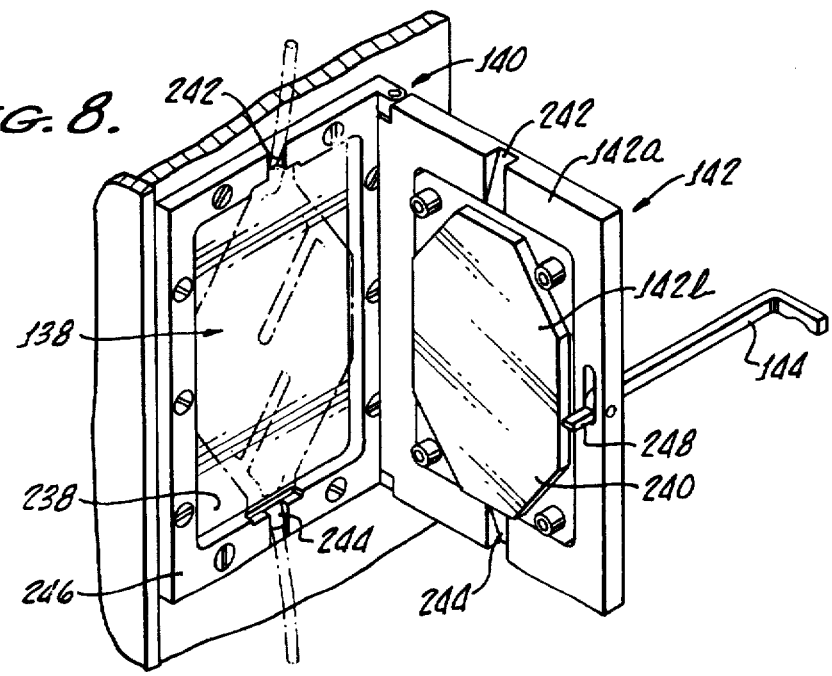

FIG. 7 provides another diagrammatic representation of the mechanism of the machine seen in FIG. 1; and FIG. 8 provides the other front quarter perspective view of the machine seen in FIG. 1, and is taken from the other side and without the disposable apparatus set seen in FIGS. 1 and 2 in order to better depict salient features of the invention.

DETAILED DESCRIPTION OF AN EXEMPLARY PREFERRED EMBODIMENT OF THE INVENTION

An Overview

Viewing first FIGS. 1 and 2 in conjunction with one another, a combined apparatus for magnetic separation of cells is generally indicated with the numeral 10. This combined apparatus 10 includes a semi-automated machine 12, and a disposable and replaceable apparatus set 14. The disposable apparatus set 14, and the machine 12 are constructed and configured to be used together in cooperation to carry out a semi-automated magnetic separation of target cells, as will be further explained. Following a magnetic target cell separation process, the disposable apparatus set 14 is removed from the machine 12 and is discarded. Thereafter, another substantially identical disposable apparatus set 14 is installed on the machine 12 in preparation for a next subsequent magnetic cell separation.

Disposable Apparatus Set 14

The disposable apparatus set 14 is shown in FIG. 1 installed on the machine 14. However, in order to gain a better understanding of this disposable apparatus set 12, and of its use in the process of magnetic cell separation in conjunction with the machine 12, attention is directed now to FIG. 2. The disposable apparatus set 14 includes a non-collapsible shape-retaining transparent cylindrical primary container 16. It is understood that the primary container of the invention may have an alternative geometrical form other than a cylinder, such as a generally rectangular volumetric form. This primary container 16 includes a transparent tubular body 18 having upper and lower end walls 20 and 22, respectively, which are sealingly joined permanently to the body 18 in order to define a primary processing chamber 24. Along the vertical length of the tubular body 18 are disposed three level marks, respectively indicated with the indicia "B", "A", and "L", from bottom to top of the chamber 24. These indicia will be used by a human attendant of the machine 12 to judge volumes of liquid combined with other materials (such as cells and paramagnetic beads) in the chamber 24 during the cell separation process, and especially during the adding of certain liquid materials to the contents of the chamber 24.

Permanently attached at the upper wall 20, and communicating with the chamber 24, is a vertically extending vent tube 26. This vent tube 26 extends to and carries a vent filter 28. On the vent tube 26 is carried a vent control clamp 30, which is effective to collapse and close the tube 26, as well as to allow this tube to open due to its own elasticity when the clamp 30 is released to allow venting of chamber 24. Also permanently attached on the upper wall 20, and communicating with the chamber 24, is an injection fitting 32, which includes a penetrable septum (not shown) to allow for injection of material into the chamber 24 through the septum via use of a hypodermic needle and syringe.

At the bottom wall 22, and communicating with the chamber 24, is permanently connected a short length of flexible tubing 34. This flexible tubing 34 extends to and is permanently joined to a y-connector 36. From the y-connector 36 extends a pair of permanently connected tubes 38 and 40. The tube 40 defines an outlet drain line for the disposable apparatus 14, and carries a permanently attached spike connector 42. On the drain line 40 is carried a roller clamp 44, which is effective to close communication from the chamber 24 to the drain outlet 42 by collapsing the tube 40, and to allow this tube to open also. The tube 38 extends to a permanently attached y-connector 46, and a roller clamp 48 controls communication through the tube 38. From the y-connector 46 extends two permanently attached tubes 50 and 52. The tube 50 communicates with a pair of inlet spike connectors 54, and 56, via a permanently connected y-connector 58, and a pair of tubes 60, and 62 connected permanently thereto. On the tubes 60 and 62 are carried respective roller clamps 64, and 66 to control communication through these tubes.

The tube 52 extends to a permanently attached secondary container 68. A respective roller clamp 70 controls communication through the tube 52. The secondary container 68 is formed as a flexible bag of octagonal shape as seen in the viewing aspect of FIG. 2. This container has a pair of transparent closely-spaced and generally flat walls, indicated with the numerals 72, and 74, which are both generally one behind the other and in the plane of the Figure as seen in FIG. 2. These confronting walls are joined at their octagonal periphery in confronting relation only slightly spaced apart in the direction perpendicular to the plane of the Figure to define a thin envelope-like shape for a secondary chamber 76. Within the container 68, the walls 72, 74 define respective ribs 78 which extend toward one another and are inter-bonded together to form a pair of angulated partitions, indicated with the numeral 80, within the chamber 76. Because of the partitions 80, the chamber 76 forms a serpentine flow path therethrough, which is indicated with the numeral 82, viewing FIG. 2.

It should be noted that the apparatus 14 is presented in FIG. 2 as though it were laid out on a table, and that in the use of the machine 12 and apparatus 14, the flow path 82 extends upwardly through the chamber 76 so that fluid flow, and flow of material carried into chamber 76 by the flowing fluid, is against gravity. The importance of this flow against gravity in the chamber 76 will be explained further.

From the secondary container 68 a permanently attached tube 84 extends to a y-connector 86, which is also permanently attached to the tube 84 and to a pair of tubes 88, and 90. The tubes 88 and 90 respectively extend to a product outlet luer lock fitting 92, and to a product outlet ring cap fitting 94. Respective roller clamps 96 and 98 control the communication in tubes 88 and 90.

Machine 12

Having observed the structure of the disposable apparatus set 14, attention may now be directed again to FIG. 1, in which this disposable apparatus set is shown installed on the machine 12 preparatory to the conducting of a magnetic cell separation process with the combined apparatus 10. As is seen in FIG. 1, the machine 12 includes a housing 100 having a base portion 102 and a vertically upwardly extending tower portion 104 upon the base 102. Telescopically received in the housing 100, and extending adjustably upwardly therefrom, is a T-shaped bag hanger 106. This bag hanger 106 is adjustable for vertical position of a cross bar portion 108 thereof by sliding a shaft portion 110 of the bag hanger 106 up or down relative to the tower portion 104, as is indicated by the arrow 112, and locking a selected position by use of a manual locking screw threadably carried by the housing 100 (not visible in the drawing Figures). The contoured external knob 116 of this locking screw is seen projecting from the front of the tower portion 104.

Upon the cross bar 108 are carried two bags 118, 120, one of prepared cell suspension and the other of buffering solution, respectively. The bags 118 and 120 are connected to the disposable apparatus set 14 at the inlet spike connectors 54 and 56. The primary container 16 is carried in upper and lower clamp features 122, 124, respectively, of a rocker assembly 126, which is journaled on one side of the tower 104. The rocker assembly 126 is pivotal about a pivot axis, generally indicated at 128, and as indicated by arrow 130, between the vertical position shown in FIG. 1, and a limit position about 120 degrees clockwise from the vertical position, as will be further explained. The lower clamp feature 124 on the rocker assembly 126 takes the form of a cup-like bracket 132 extending outwardly from the rocker assembly 126 and having a slot for passage of the tube 34. The upper clamp feature 122 takes the form of an arcuate saddle member 134 disposed near the upper extent of the rocker assembly 126 for engaging the tubular body 18, and a spring-loaded cooperative latch arm 136 for retaining this first container 16 in engagement with the bracket 132 and saddle 34.

On the front surface of the tower 104 is carried a secondary magnet assembly 138 and holder 140 for the secondary container 68. This holder 140 includes a door assembly 142, having a metallic frame portion 142a, defining a central opening within which is carried a transparent window portion 142b. The door 142 is provided with a pivotal door handle mechanism 144, both of which are visible in the depiction of FIG. 1. The secondary container 68 is inserted into the holder 140, with the tube 52 extending into this holder via a lower notch (not seen in drawing FIG. 1), and the tube 84 extending outwardly from this holder via an upper notch (also not visible in FIG. 1). The tube 38 is sufficiently long in conjunction with the length of tube 34 to extend to the bottom of the first container 16, and to allow the movements of this chamber on rocker 126 through the full range of pivotal movement for this rocker assembly, as is described below.

At a front inclined panel 146 of the housing base 102 is disposed an operator annunciator screen 148, and input keypad 150. The annunciator screen 148 is preferably of a liquid crystal alpha-numeric type so that commands, signals, and directions to a human operator can be spelled out, and so that numerical values, such as count-down times, can be displayed for the operator. This front panel 146 also includes an audible alert-signal generator, such as a buzzer indicated with the arrow 152, for sending an auditory signal to the human attendant operator when a particular phase of the process is complete, or when a part of the process to be performed by a human attendant is required, for example. The human attendant will then silence the buzzer by an input to the key pad 150, and read the annunciated directions from the screen 148. It should be noted that the machine 12 can signal the operator for attendance either by an auditory signal, or simply with an annunciated signal or direction on screen 48. Above the inclined front panel 146, the housing base 102 carries a pair of upright tubing supports 154, which are used to organize and position the various tubes of the disposable apparatus set 14. Adjacent to the machine 12 is positioned a product container 156, which communicates with one of the product outlet fittings 92, 94. A waste container, depicted in FIG. 1, and referenced with the numeral 42a, may preferably be connected to the waste drain connection 42.

Figure 3:
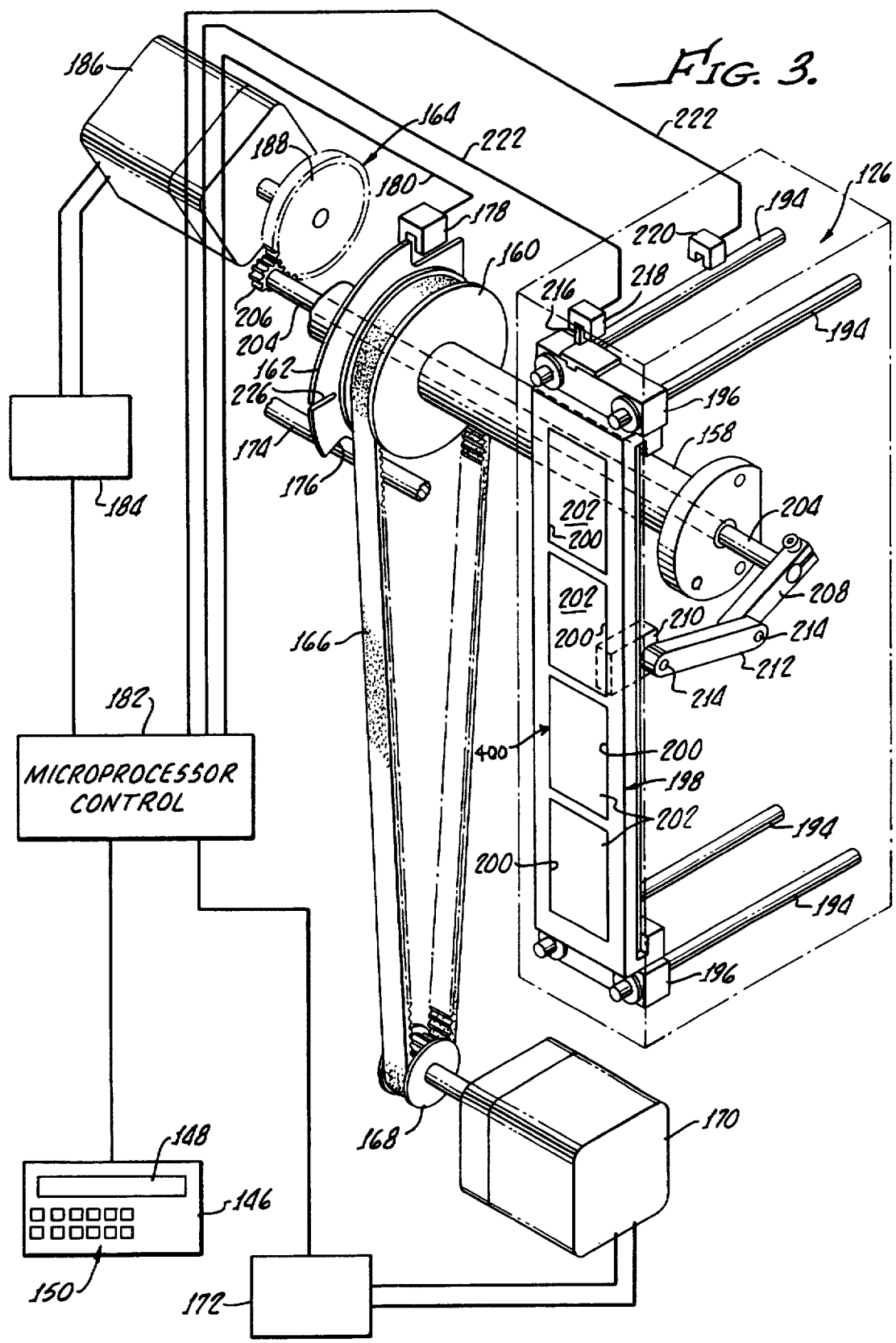

Turning now to FIG. 3, a diagrammatic representation of the mechanization of the machine 12 is presented. As is seen in FIG. 3, the tower portion 104 journals a tubular shaft member 158. The shaft member 158 carries the rocker assembly 126, and also drivingly carries a toothed pulley 160, an angular encoder and stop disk 162, and a mechanism, generally indicated with the numeral 164, for holding and positioning a primary magnet assembly 400 (which is further described below). From the toothed pulley 160, a toothed timing belt 166 extends to a toothed pulley 168 which is drivingly carried on the output shaft of a motor 170. The pulleys 160, 168, in cooperation with the toothed belt 166 define a positive 3:1 gear ratio between the motor 170 and the rocker assembly 126. The motor 170, along with a motor controller 172 for this motor, is carried within the base portion 102 of the housing 100. The shaft member 158 defines the pivotal axis 128 for the rocker assembly 126, so that rotation of this shaft by the belt 166 and pulleys 160, 168 driven by motor 170 pivots the rocker assembly between its various positions, is effective to hold a selected position for the rocker assembly 126 because of magnetic cogging of the motor 170, and is effective also to angularly oscillate the rocker assembly 126 about the axis 128 so as to agitate or mix the contents of the primary container 16.

Within the tower portion 104, the housing 100 carries a stop rod 174, which is engagable by an edge surface 176 of the angular encoder and stop disk 162 when the rocker assembly 126 is rotated counter clockwise about the axis 128 (viewing FIGS. 1 and 3) substantially to the vertical position seen in these Figures. A sensor 178 is also carried by the housing 100 within tower portion 104, and is connected by appropriate conductors 180 to a microprocessor-based controller, indicated with the numeral 182. This microprocessor-based controller 182 also has connection with the motor controller 172, and with another similar motor controller 184. The motor controller 184 controls a gear-head stepper motor 186, which drivingly carries on an output shaft thereof a gear 188 forming a part of the mechanism 164. The microprocessor-based controller 182 also has a connection with the annunciator panel 146 and key pad 148, as is diagrammatically indicated viewing FIG. 3.

Figure 4:
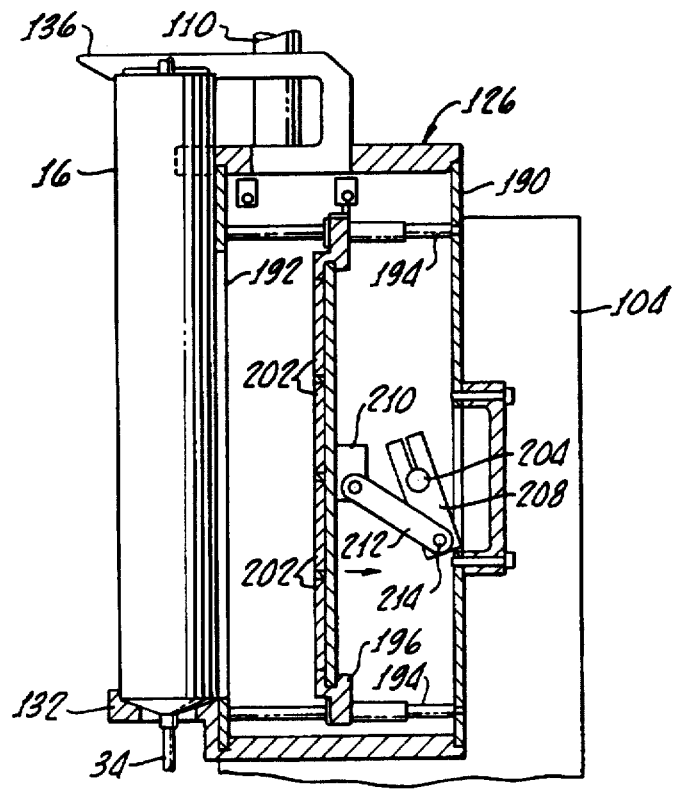

More closely considering the mechanism 164 for moving a primary magnet assembly 400, it is seen that the rocker assembly 126 consists of a hollow box-like housing 190, which is seen in phantom in FIG. 3. The housing 190 defines a front opening 192, which is best seen in FIGS. 1 and 4. Within the hollow housing 190, four guide rods 194 extend from front to back of this housing outside of the boundaries of the opening 192. Slidably carried on the guide rods 194 is a primary magnet frame member 196. This frame member 196 on a protruding portion 198 thereof defines four magnet windows 200 within which respective primary permanent magnets 202 are captured to form a primary magnet assembly 400.

Suitably, each primary permanent magnet 202 is made of a high magnetism alloy of neodymium, iron, and boron, obtainable from the Crucible Magnetics Co., of Elizabethtown, Kentucky. Each primary permanent magnet 202 has a magnetic field strength at its surface of preferably 2,000 to 2,700 gauss, most preferably 2,100 to 2,600 gauss. The primary permanent magnets 202 may be assembled with any combination of north or south poles facing inwards or outwards to form a primary magnet assembly 400. When the poles of each primary permanent magnet are arranged so that either all south poles face outwards, or so that all north poles face outwards, the primary magnet assembly 400 has a magnetic field strength of preferably about 3,000 gauss at a surface near either end of the primary magnet assembly 400, and a magnetic field strength of about 2,100 gauss to about 2,600 gauss at a surface near the middle of the primary magnet assembly 400. When the primary permanent magnets 202 are arranged with alternating south and north poles facing outwards, the primary magnet assembly 400 has a magnetic field strength of about 4,000 gauss at a surface near an interface between north and south poles. It is within the scope of this invention to arrange the primary permanent magnets 202 with any permutation of north and south poles facing inwards or outwards to provide a primary magnet assembly 400 having magnetic field characteristics advantageous for different types of magnetic cell selection. It will be apparent to those ordinarily skilled in the pertinent arts that the primary magnets 202 have a certain limited magnetic flux "reach out" distance.

Figure 6:
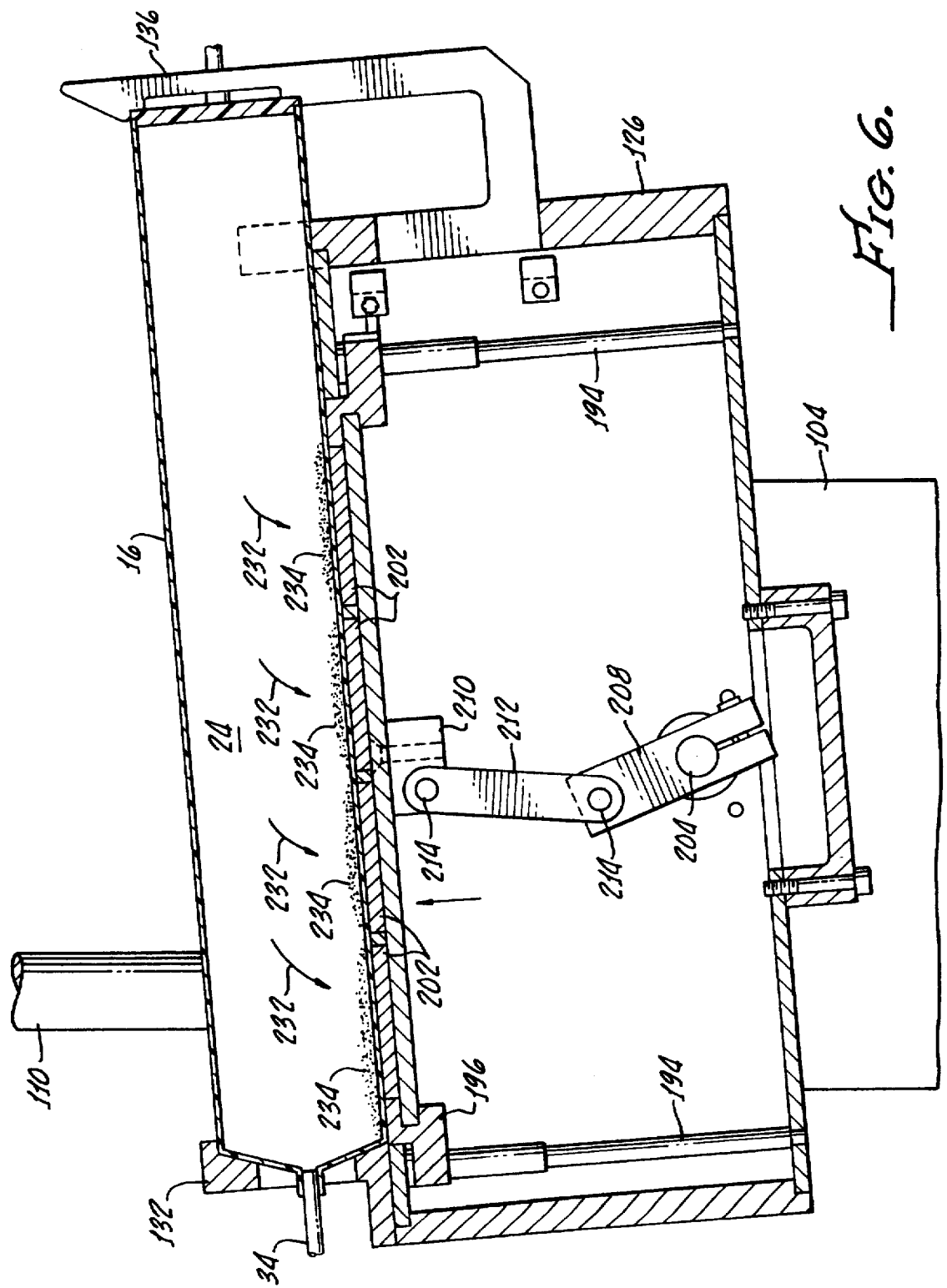
FIG. 6 is a diagrammatic fragmentary representation of a portion of the machine seen in FIG. 1, and depicts the machine portion selectively positioned for carrying out a step in the process of magnetic positive cell separation.

In a first or advanced position of the primary magnet frame member 196, the portion 198 thereof extends through the opening 192, so that the primary magnets 202 are substantially flush against the tubular body member 18 of the primary container 16 of disposable apparatus set 14. This first position for the primary permanent magnets 202 is seen in FIGS. 1, 3, and 6.

Figure 5:
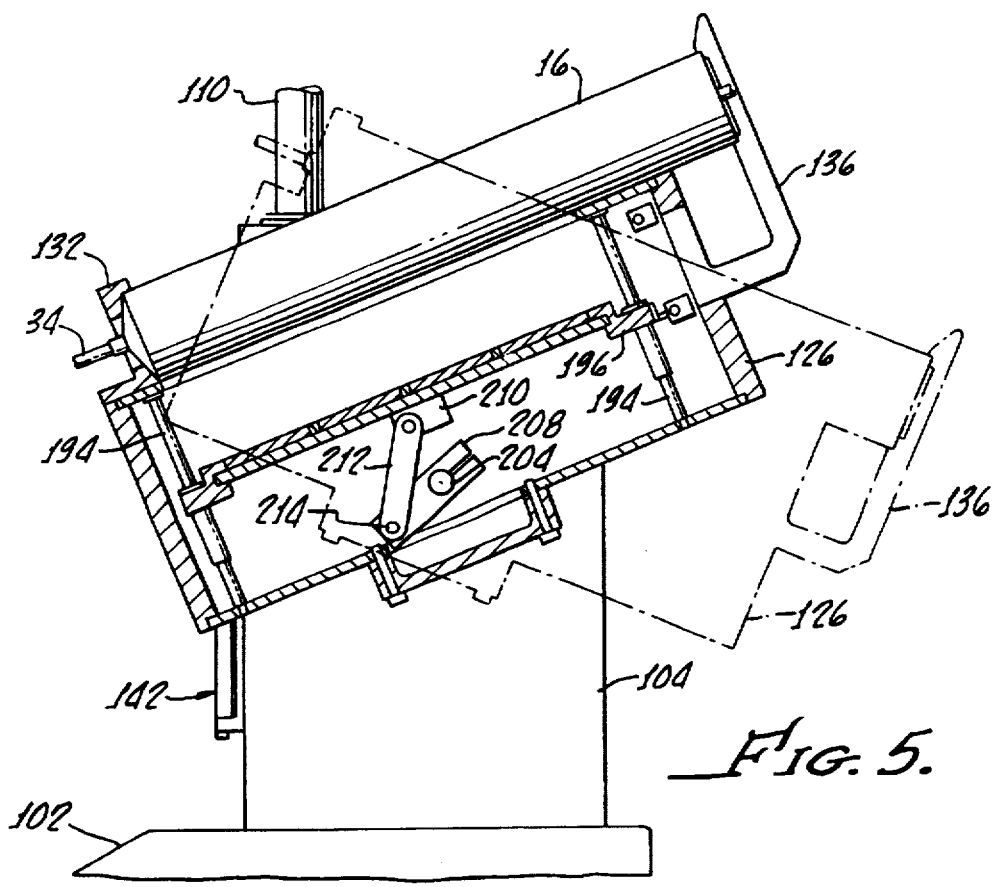
FIG. 5 is a diagrammatic fragmentary representation of a portion of the machine seen in FIG. 1, and depicts in solid and phantom lines the oscillating rocking motion which is provided by the machine.

In order to move the primary magnet frame member 196, and the primary permanent magnets 202 carried thereby, from the first advanced position illustrated in FIG. 3, to a second or retracted position, seen in FIGS. 4 and 5, the mechanism 164 includes a shaft 204 journaled within the tubular shaft member 158. This shaft 204 carries a gear 206 meshing with the gear 188 of motor 186, and also carries an actuator arm 208 disposed within the rocker housing 190 behind the frame member 196. Between the distal end of the actuator arm 208 and a bracket 210 attached to the frame member 196 extends a link member 212. This link member 212 is pivotally connected to each of the actuator arm 208 and bracket 210 via associated pivot pins, generally indicated with the numeral 214. Consequently, when the shaft 204 is rotated counter clockwise, viewing FIG. 3, by motor 186, and meshing gears 188, and 206, the actuator arm 208 pulls the frame member 196 and primary permanent magnets 202 away from the primary container 16 to the position indicated in FIG. 4. Of course, opposite pivotal movement of the shaft 204 and actuator arm 208 advances the primary permanent magnets 202 to the position seen in FIGS. 1 and 3.

As will be further explained, the motor 186, and mechanism 164 are pivotal with the tubular shaft 158 and rocker member housing 190 so that pivotal movement of the rocker assembly 126 has no effect upon and is independent of the position of the magnet frame 196 and primary permanent magnets 202 relative to the primary container 16. Also seen in FIG. 3 is a flag member 216 which is carried by and extends upwardly from the frame member 196. This flag member 216 is sensed by one or the other of two sensors 218, 220 in the respective advanced and retracted positions of the frame member 196. Each of the sensors 218, 220 has connection with the microprocessor-based controller 182 via appropriate conductors 222. Accordingly, the controller 182 will operate the motor 186 in the appropriate direction to move the primary permanent magnets 202 between their advanced and retracted positions. The primary permanent magnets 202 only occupy a position between their advanced and retracted positions while they are moving in traversing between these two positions. The primary permanent magnets 202 are not stopped at positions other than their advanced position or retracted position.

Method of use of Machine 12 and Disposable Apparatus Set 14

Having now gained a general understanding of the machine 12 and disposable apparatus set 14, which together make up the combined apparatus 10, attention may now be directed both to additional structural features of the machine 12, which will be described in conjunction with a description of how the machine 12 and apparatus set 14 are used together in carrying out a process of magnetic cell separation.

Viewing FIGS. 1 and 4, it is seen that with the rocker assembly 126 in its vertical position, and with the primary magnets 202 retracted, a first phase of the magnetic cell separation process may be started by adding into the primary chamber 24 a small amount of the buffer solution from bag 120 and the cell mixture from bag 118. After emptying bag 118 into the primary chamber 24, the human operator may, if desired, flow a small amount of the buffer solution from bag 120 into bag 118 and then into the chamber 24 to rinse remaining cells from the bag 118 into the chamber 24. Buffer solution is then added to chamber 24 to bring the liquid level therein to one of the specified level lines. Into the chamber 24 via the injection port 32 is then placed a calculated quantity of paramagnetic beads. All of the clamps controlling liquid flow into and out of the primary chamber 24 are then closed.

When the operator indicates to machine 12 by an appropriate input at key pad 150 that this first preparatory activity is completed, the microprocessor based controller 182 moves the rocker assembly 126 from the vertical position shown in FIGS. 1 and 4 through a first agitation position (which is illustrated by the solid line position seen in FIG. 5), on through the horizontal position, and beyond this horizontal position to a second agitation position (seen in phantom lines in FIG. 5). This first agitation position of the rocker assembly 126 is preferably about 22.5 degrees short of a horizontal position for the container 16, while the second agitation position is 22.5 degrees beyond the horizontal with respect to the vertical position for primary chamber 16 which is seen in FIG. 1. The way by which the machine 12 locates these angular first and second agitation positions is described below. However, the operator can pre-program the controller 182 to employ another first agitation position for the rocker assembly 126 if desired. The machine 12 is configured to allow a first agitation position which is any where in the range from just short of the horizontal to 30 degrees from horizontal. From the first agitation position, the machine 12 pivots the rocker assembly 126 clockwise viewing FIG. 5, through the horizontal, and to an equivalently-angulated second agitation position, which is shown in phantom lines in FIG. 5.

During a selected time interval, the machine 12 continuously oscillates the primary container 16 back and forth between the first and second agitation positions shown in FIG. 5 at a rate which is also variable and may be preprogrammed. Of course, each oscillation of the primary container 16 causes the liquid contents of this container to flow or surge back and forth from end to end of the chamber 24, thoroughly agitating and mixing the contents of this primary chamber. This initial agitation interval results in the appropriately coated paramagnetic beads binding to all or substantially all of the target cells in the chamber 24. This rocking of the primary container 16 and agitation of the contents of chamber 24 is achieved by repeated reversals of the direction of rotation of motor 170. During this time, the primary magnets 202 are retracted into the housing 190 so that the magnetic field from these magnets does not affect the paramagnetic beads.

Attention now to FIG. 7 will assist the reader in understanding how the controller 182 is enabled to control the rocker assembly 126 to locate the vertical position for this assembly, to locate the first and second agitation position, and to position this rocker assembly in a separation position which will be described. FIG. 7 presents another somewhat diagrammatic representation of the mechanization of the machine 12, but is taken from the opposite side from the view of FIG. 3, with the rocker assembly 126 also in the vertical position. Viewing FIG. 7, it is seen again that in the vertical position for the rocker assembly, the edge surface 176 of disk 162 confronts the stop rod 174, but preferably does not actually contact this stop rod. Also, at the vertical position, the sensor 178 is just clear of an edge 224 of the encoder/stop disk 162. When the motor 170 pivots the rocker assembly 126 counter clockwise viewing FIG. 7 (clockwise viewing FIGS. 1 and 3) to the horizontal position, a slit 226 in the encoder/stop disk 162 aligns with and is sensed by the sensor 178. From this horizontal position, the controller 182 pivots the rocker assembly back toward but just short of contact of the edge 176 with rod 174. This is the vertical position for the rocker assembly 126.

The motor 170 is preferably a stepper type of motor with a full-step rotation of 1.8 degrees of shaft rotation, and a half-step capability (i.e., the motor 170 can be commanded by controller 182 to rotate its output shaft in full-step units of 1.8 degrees of shaft rotation, or half steps of 0.9 degrees may also be commanded). In view of the 3:1 gear ratio between the motor 170 and shaft 158 which carries the rocker assembly 126, the controller 182 is programmed with the information that one step of the motor 170 equals 0.6 degrees of pivotal motion for the rocker assembly 126 (half-steps being equal to 0.3 degrees of motion). The controller 182 in an initial calibration phase of operation of the machine 12 will pivot the rocker assembly 126 from the horizontal position back toward contact between rod 174 and edge 176, stopping the rocker assembly just short of this contact. Thus, no matter what position the rocker assembly 126 happens to be in when the machine 12 is turned on and a calibration phase is conducted, the controller will thereafter have a reference for the horizontal position by reference to the slit 226, and can locate other positions for the rocker assembly 126 by counting steps and half steps for motor 170.

During rocking of the rocker assembly 126, the controller 182 counts the number of steps for motor 170 away from and back to the horizontal position, and this reference position is updated each time the slit 226 aligns with the sensor 178. The total angle through which the rocker assembly 126 is tilted during rocking is variable by the controller 126. As may be further explained, if the operator for the machine 12 commands that the rocker assembly be rocked through 50 degrees, for example, in order to agitate the contents of the container 16, then the controller 182 divides 50 by 2, and divides the result (25) by the 0.6 degree value for a full motor step. The closest integer value for the result (42), is the number of steps in each direction from the horizontal reference position (referenced to slit 226) which the controller 182 will command for the motor 170.

The preferred position of rocker assembly 126 for an initial phase of magnetic capture separation is about 5 degrees from the horizontal, and is also determined by reference to the horizontal reference position. The 0.6 degree per motor step value is divided into the preferred angular position for the rocker assembly to obtain a closest-integer value for the number of steps for the motor 170 to move the rocker assembly 126 from the horizontal position to the first magnetic capture position seen in FIG. 6.

FIG. 7 also shows that the mechanism 164 includes a motor mount housing 228 carried on the tubular shaft 158 for pivotal movement therewith. The tubular shaft 158 defines a window 230, at which the gear 206 is exposed. The gear 188 drivingly carried by the motor 186 meshes with the gear 206, and the motor 186 is secured to the housing 228 for pivotal movement with shaft 158. This motor mount housing 228 will preferably allow an angular movement for the rocker assembly 126 of about 30 degrees beyond the horizontal position before the motor mount housing 228 strikes the stop rod 174. Accordingly, the rocker assembly 126 may be rocked alternately in each opposite direction from the horizontal position about thirty degrees for symmetrical rocking motion, if desired. This larger 30 degree angle of rocking motion would require that the motor 170 make 50 steps between horizontal reference position and each extreme of tilting motion for the rocker assembly 126. Of course, a smaller angle of rocking for the rocker assembly 126 may be selected by appropriate programming of the controller 182.

Preferably, the slit 226 is positioned 30 degrees from the edge 176 of the encoder/stop disk 162. In the event that the operator of the machine 12 selects a rocking angle for the rocker assembly 126 which is 30 degrees, or close to this value, then the edge 176 will align with the sensor 178 when the rocker assembly 126 reaches its second agitation position of 30 degrees beyond the horizontal to provide a warning to the controller 182 that the motor housing 228 is close to the stop rod 174. The controller 182 will continuously update the position of the rocker assembly 126 with respect to the horizontal, and also receives a warning from the sensor 178 when the edge 176 reaches this sensor so that a collision between the motor housing 228 and the stop rod 174 does not occur during rocking agitation of the primary container 16.

Upon completion of the selected agitation interval, the controller 182 brings the rocker assembly 126 to a stop at an initial separation position for magnetic capture of the paramagnetic beads (and bound target cells) in the chamber 24. This initial separation position, or initial position for magnetic capture, is preferably about 5 degrees counter clockwise from the horizontal, viewing FIG. 6. The primary magnets 202 are then advanced by operation of the motor 186 and mechanism 164, under the control of the controller 182. This separation position is held for a time interval which is preferably about 30 second, although another time interval of initial magnetic capture may be selected.

Immediately thereafter, the rocker assembly 126 is moved by controller 182 to a secondary separation position with the primary permanent magnets 202 remaining in the advanced position seen in FIG. 6. This secondary separation position is substantially vertical, as is seen in FIG. 1. The applicants have found this two-phase separation process, which uses an initial inclined separation position for magnetic capture of the target cells and bound paramagnetic beads from the liquid in chamber 24, advantageously spreads out the liquid contents of the chamber 24 along the length of the primary permanent magnets 202 during the first phase of separation. As is indicated in FIG. 6, the bound target cells tend to move as indicated by the arrows 232 into clumps on the wall of container 16, which clumps are indicated with the lead line and numeral 234. It will be noted that unbound paramagnetic beads and some non-target cells may also be captured in the clumps 234. At this point, after the container 16 has been moved to its second separation position, and a second separation interval of time has passed, the operator is signaled by the machine 12 to vent and drain the chamber 24. Most of the non-target cells, and the liquid from bag 118 which carried these cells, is drained from the chamber 24 into a waste container 42a.

The operator then begins the first wash of what may be a series of similar washing activities for the bound target cells from the clumps 234. That is, the chamber 24 is partially filled with buffer solution and is re-closed. The operator signals to machine 12 via key pad 150 that the primary processing container 16 is ready for further processing. Then the controller 182 retracts the primary permanent magnets 202 to release the bound cells into the fresh buffer solution in chamber 24. The machine 12 agitates container 16 between the first and second agitation positions for a preselected time interval, and then magnetically separates the bound target cells into fresh clumps on the wall of container 16 as explained above.

These fresh clumps are like the clumps 234, but are of greater purity with respect to exclusion of non-target cells and other materials in the clumps. Again, the machine 12 completes the magnetic cell separation by capturing the bound target cells into clumps on the wall of container 16, moves the rocker assembly 126 to the vertical position for a secondary separation interval, and signals the operator to attend to draining the chamber 24. If another wash and separation cycle is to follow, the operator is instructed by an indication on the annunciator screen 148 to replenish the chamber 24 with fresh buffer solution. Preferably, the target cells are subjected to three wash/separation cycles so that at the completion of these wash/separation cycles the chamber 24 contains substantially only target cells bound on paramagnetic beads, and unbound paramagnetic beads.

When the wash/separation cycles are completed, the operator is instructed to refill the primary chamber 24 with buffer solution, and to inject via port 32 a releasing material such as the enzyme chymopapain. Chymopapain releases the target cells from the paramagnetic beads by enzymatic digestion of the proteins which mediate the binding of cells to beads. Alternative means of release are within the scope of this invention. For instance, other releasing materials could include small peptides, proteins, or other molecules which compete for binding at the antibody/antigen binding sites which mediate the binding of cells to beads. As another example for releasing means, the binding of cells to beads might be mediated by biotin/avidin binding, by biotin/antibiotin binding, or by biotin analog/anti-biotin binding. In this latter example, the releasing material would be biotin.

The chamber 24 is again closed, and the machine 12 agitates the contents of the container 16 to incubate the bound target cells with the enzyme or other releasing material and to release all or substantially all of the target cells from the paramagnetic beads. At the completion of this agitation, the magnets 202 are advanced and the two-phase magnetic capture and separation procedure is repeated. However, this separation step captures the paramagnetic beads on the wall of the container 16, while the unbound target cells remain free in the buffer solution. The operator is again signaled to perform the next step of the process.

The operator is instructed by the annunciator panel of machine 12 to drain the primary chamber 24 into a product-receiving container 156, viewing FIG. 1, via the secondary chamber 76. The secondary magnet 138 has a magnetic field strength at its surface of at least about 7,000 gauss, and thus firmly traps in the secondary chamber 76 any paramagnetic beads which escape from the primary chamber 24. The flow through chamber 76 is against gravity, which also assists in insuring that no beads pass through the chamber 76. Consequently, the product delivered to container 156 is rich in target cells and is substantially devoid of non-target cells and of paramagnetic beads.

Again, the operator will be instructed by annunciator panel 148 to partially refill the primary chamber 24 with buffer solution, and the machine 12 will conduct another agitation period during which target cells caught in the clumps of paramagnetic beads will be released into the buffer solution. Following this agitation interval, the primary permanent magnets 202 will again be advanced, and a separation interval in the separation position of FIG. 6 will capture the paramagnetic beads. The operator will again be summoned to drain the chamber 24 into the product-receiving container 156 via the secondary chamber 6. Again the paramagnetic beads will be trapped on the wall of container 16 or in the secondary container 68 while the target cells are delivered to container 156 so that the product yield of target cells is increased. Preferably, this washing of the paramagnetic beads in the primary chamber 24 to free additional target cells, which are subsequently added to the collection in container 156, is conducted at least once, but may be repeated several times if desired.

Attention now to FIG. 8 will show that the secondary magnet 138 and holder 140 for the secondary container 68 cooperatively define a recess 238 for receiving the secondary container 68. The secondary magnet 138 defines a planar back wall for this recess 238, while the window portion 142*b* of the door assembly 142 defines a protruding hexagonal portion 240 extending into this recess 238 toward but short of the back wall defined by the secondary magnet 138. This portion 240 in cooperation with the back wall of the recess 238 defined by the secondary magnet 138 ensures that the secondary container 76 maintains a flat and thin configuration in close proximity to the secondary magnet 138 to ensure complete capture of paramagnetic beads passing into the secondary chamber 76.

The notches 242,244 which were mentioned earlier as allowing passage of the tubes 52 and 84 into the holder 140 are seen to be defined in part by the frame portion 142a of the door 142, and in part by a rim 246 of the holder 140. The notches 242, 244 open across the rim 246 of the holder 140 into the recess 238. On the door 142 the door handle 144 includes an inwardly extending cam portion 248, which engages the underlying portion of the rim 246 when the outer part of the handle 144 is lifted to lever open the door assembly 142 in opposition to the strong magnetic field from the secondary magnet 138. Because a part of the door assembly 142 is made of magnetic metallic material, no other latching of the door is required. Further, the notches 242,244 defined in the frame portion of the door assembly 142 can be used to receive the tubing sections 52 and 84 adjacent to the secondary container, holding this container to the protrusion 240 while the door 142 is closed.

Also, the levering action provided by the handle 144 and cam portion 248 is of assistance in moving the door frame 142a far enough away from the strong magnetic field of the secondary magnet 138 to allow the door 142 to be easily opened by hand. This configuration of the door 142 and door handle 144 with cam portion 248 also has an important advantage when installing the secondary container 62 into the recess 238. As mentioned above, the secondary container 62 is made essentially like a flat envelope or bag of transparent plastic sheet material. When this container is placed into the recess 238 and the door 142 is closed, there is an increasingly strong pull on the door by the secondary magnet 138. However, the door 142 should not be allowed to slam shut under this magnetic pull. Accordingly, the cam action of the handle 144 allows the operator to slowly close the door 142 while insuring that the container 62 is properly positioned in recess 238, and is not pinched.

While the present invention has been depicted, described, and is defined by reference to a particularly preferred embodiment of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiment of the invention is exemplary only, and is not exhaustive of the scope of the invention. Consequently, the invention is intended to be limited only by the spirit and scope of the appended claims, giving full cognizance to equivalents in all respects.

We claim:

1. Apparatus for magnetic cell separation using paramagnetic microbeads and a container set including a primary container which is substantially of elongate cylindrical shade and a secondary container, which containers may be placed in fluid communication with one another, and which containers are magnetically permeable, said apparatus comprising:

a base member, said base member movably supporting an agitation member, and first power drive means for agitating said agitation member relative to said base member;

said agitation member including means for removably securing thereto in a relatively fixed secured position the primary container within which a liquid suspension of the cells and microbeads may be agitated by movement of said agitation member; said agitation member further movably carrying a primary magnet for movement between a first magnet position adjacent to the primary container in its secured position, in said first magnet position of said primary magnet magnetic flux penetrating the primary container in its secured position to attract and capture the microbeads, and said primary magnet being movable to a second magnet position spaced from the primary container in its secured position so that magnetic flux from said primary magnet does not capture the microbeads; and second power drive means for selectively moving said primary magnet between said first end second magnet positions independently of agitation of said primary container:

wherein said base member further includes a holder for a secondary container, and a secondary magnet disposed adjacent to said secondary container when the latter is held on said holder for capturing paramagnetic microbeads which escape from said primary container;

wherein said base member pivotally carries said agitation member; and wherein said agitation member is configured to secure thereto in a fixed relative position the primary container, said first power drive means also being effective to tiltingly move said agitation member and primary container between a first agitation member position in which the length of the primary container is vertical, and a second agitation member position in which the length of the primary container is horizontal.

2. The apparatus of claim 1 wherein said power drive means includes means for affecting successively opposite tilting movements of said agitation member and primary container from said horizontal second agitation member position.

3. The apparatus of claim 1 wherein said first power drive means includes a first stepper motor, and a motor drive controller for said first stepper motor.

4. The apparatus of claim 1 wherein said second power drive means includes a second stepper motor, and a motor drive controller for said second stepper motor.

5. The apparatus of claim 1 wherein said first power drive means is effective to also move said agitation member and primary container to a first separation position in which said agitation member and the primary container are angulated relative to said horizontal second agitation member position.

6. The apparatus of claim 5 wherein said first separation position is angulated relative to said horizontal agitation member position by a certain angle.

7. The apparatus of claim 6 wherein said certain angle is substantially 5 degrees.

8. The apparatus of claim 1 further including control means for controlling operation of said first and said second power drive means.

9. The apparatus of claim 8 wherein said control means includes a microprocessor-based controller, and said apparatus including an annunciator screen upon which said controller can further provide output information to a human operator of said apparatus.

10. The apparatus of claim 9 wherein said apparatus further includes an operator input device by which said human operator can make an input to said microprocessor-based controller.

11. The apparatus of claim 8 further including sensor means for indicating to said control means when said agitation member is in said first agitation member position and when said agitation member is in said second agitation member position.

12. The apparatus of claim 11 wherein said sensor means includes an encoder disk rotating with said agitation member, said encoder disk having at least one feature which is distinguishable from the remainder of said encoder disk, and at least one sensor device responsive to said at least one feature and providing an input to said control means in response to alignment of said feature with said sensor device.

13. The apparatus of claim 12 wherein said encoder disk has a first feature which aligns with said sensor device when said agitation member is in said first agitation member position, and a second similar feature which aligns with said sensor device when said agitation member is in said second agitation member position.

14. The apparatus of claim 8 further including sensor means for indicating to said control means when said primary magnet is in said first magnet position, and when said primary magnet is in said second magnet position.

15. The apparatus of claim 14 including a flag member carried with said primary magnet between said first and said second magnet positions, and respective first and second sensor devices responsive to alignment of said flag member therewith to providing a respective input to said control means.

16. Apparatus for performing magnetic cell separation using both paramagnetic microbeads and a container set including an elongate primary container in which cells and paramagnetic microbeads are receivable in liquid mixture, and a secondary container, which first and second containers of said container set are magnetically permeable and may be placed in fluid flow communication with one another, said apparatus comprising: a base having a tower portion extending upwardly thereon, said tower portion journaling a rocker assembly for pivotal movement about a generally horizontal pivot axis, said rocker assembly including means for securing the elongate primary container thereto in a fixed relative position, said apparatus including a first power drive means both for selectively pivoting said rocker assembly about said pivot axis and for positioning said rocker assembly in selected pivotal positions including a horizontal position and a vertical position for said primary container, a primary magnet having a certain magnetic flux reach carried on said rocker assembly and movable between a first magnet position placing said primary container in its secured position on said rocker assembly within said magnetic reach so that magnetic flux from said primary magnet is effective to magnetically capture a substantial percentage of the paramagnetic microbeads in said primary container, and said primary magnet being movable to a second magnet position spaced from said primary container in its secured position on said rocker member so that said primary container is substantially not within said magnetic flux reach to thereby magnetically release said paramagnetic microbeads to mix into the liquid in the primary container, second power drive means for selectively moving said primary magnet between said first and said second magnet positions, and control means for controlling said first and said second power drive means to selectively agitate said primary container in its secured position on said rocker assembly by opposite tilting movements of said rocker assembly about said pivot axis and to selectively magnetically capture and magnetically release said paramagnetic microbeads in said primary container by respective movements of said primary magnet between its first and second magnet positions.

17. The apparatus of claim 16 wherein said base further includes said base carrying a holder for a secondary container, and a secondary magnet disposed adjacent to said secondary container for capturing paramagnetic microbeads which escape from said primary container into said secondary container.

18. The apparatus of claim 17 wherein said holder includes a rim defining a recess into which said secondary container is receivable, a door hinged on said base for closing said recess and confining said secondary container in close association with said secondary magnet, and a handle assembly for effecting opening of said door.

19. The apparatus of claim 18 wherein said door includes a frame portion formed of magnetic material and which is attracted to said secondary magnet, said handle assembly including a camming portion which engages said rim to both cam said door open in opposition to said magnetic attraction of said door frame by said secondary magnet, and to allow said door to be controllably closed in conjunction with said magnetic attraction.

20. The apparatus of claim 16 wherein said control means includes a microprocessor-based controller.

21. The apparatus of claim 20 further including both an annunciator means for visually displaying output information from said controller to a human operator of said apparatus, and an input facility by which said human operator may provide input information to said controller.

22. The apparatus of claim 21 wherein said microprocessor-based controller is programmed with all of the steps in said magnetic cell separation, said microprocessor-based controller displaying for a human operator on said annunciator means steps in said process which said human operator is to perform.

* * * * *